(12) United States Patent
Dilleen et al.

(10) Patent No.: US 8,012,428 B2
(45) Date of Patent: Sep. 6, 2011

(54) ANALYTICAL TEST STRIP WITH MINIMAL FILL-ERROR SAMPLE VIEWING WINDOW

(75) Inventors: John William Dilleen, Alloa (GB); Lynsey Whyte, Newtonmore (GB); Robert Hamish MacLeod, Culloden (GB); Ramsay Raymond Donald Darling, Inverness (GB)

(73) Assignee: LifeScan Scotland, Ltd. (GB)

( * ) Notice: Subject to any disclaimer, the term of this patent is extended or adjusted under 35 U.S.C. 154(b) by 274 days.

(21) Appl. No.: 12/261,293

(22) Filed: Oct. 30, 2008

(65) Prior Publication Data

US 2010/0112678 A1  May 6, 2010

(51) Int. Cl.
*G01N 21/75* (2006.01)
*G01N 27/327* (2006.01)

(52) U.S. Cl. ............... 422/402; 204/403.02; 204/403.04

(58) Field of Classification Search .................. 204/403.01–403.15; 205/777.5, 205/778, 792; 422/55–58, 400–402
See application file for complete search history.

(56) References Cited

U.S. PATENT DOCUMENTS

| | | | |
|---|---|---|---|
| 5,708,247 A | 1/1998 | McAleer et al. | |
| 5,876,577 A | 3/1999 | McAleer et al. | |
| 5,935,864 A | 8/1999 | Schramm et al. | |
| 6,077,660 A * | 6/2000 | Wong et al. ................ | 435/4 |
| 6,241,862 B1 | 6/2001 | McAleer et al. | |
| 6,270,637 B1 | 8/2001 | Crismore et al. | |
| 6,287,451 B1 | 9/2001 | Winarta et al. | |
| 6,733,655 B1 | 5/2004 | Davies et al. | |
| 6,814,844 B2 | 11/2004 | Bhullar et al. | |
| 6,821,400 B2 | 11/2004 | Jaeger | |
| 6,846,453 B1 * | 1/2005 | Uesaka et al. ................... | 422/58 |
| D501,560 S | 2/2005 | Whyte et al. | |
| D512,512 S | 12/2005 | Bell et al. | |
| 7,288,174 B2 * | 10/2007 | Cui et al. ................. | 204/403.14 |
| 7,374,949 B2 | 5/2008 | Kuriger | |
| 2005/0013731 A1 * | 1/2005 | Burke et al. ................... | 422/56 |
| 2005/0016844 A1 | 1/2005 | Burke et al. | |
| 2006/0131171 A1 | 6/2006 | Kobayashi | |
| 2007/0054414 A1 | 3/2007 | Burgess-Cassler et al. | |
| 2007/0089987 A1 | 4/2007 | Neel et al. | |
| 2007/0193882 A1 | 8/2007 | Dai et al. | |
| 2008/0087543 A1 | 4/2008 | Bae et al. | |
| 2008/0114228 A1 | 5/2008 | McCluskey et al. | |

FOREIGN PATENT DOCUMENTS

EP    1600773 B1   2/2009
WO    2008/040982 A1   4/2008

* cited by examiner

*Primary Examiner* — Alex Noguerola

(57) ABSTRACT

An electrochemical-based analytical test strip includes an electrically-insulating substrate, a patterned conductive layer disposed over the electrically-insulating substrate, a patterned insulating layer disposed over the patterned conductive layer, an enzymatic reagent layer disposed over the patterned conductive layer, a patterned adhesive layer disposed above the enzymatic reagent layer and a top layer disposed over the enzymatic reagent layer. In addition, the test strip has a sample-receiving chamber defined by the electrically-insulating substrate, the patterned conductive layer, the patterned insulating layer, the enzymatic reagent layer, the patterned adhesive layer and the top layer. The sample receiving chamber of the test strip has a working portion and a non-working portion and the top layer has a first portion and an opaque second portion. The first portion is configured such that a user can view the working portion of the sample-receiving chamber through the first portion of the top layer, while the opaque second portion is configured to preclude a user from viewing the non-working portion of the sample-receiving chamber.

10 Claims, 3 Drawing Sheets

ANALYTICAL TEST STRIP WITH MINIMAL FILL-ERROR SAMPLE VIEWING WINDOW

BACKGROUND OF INVENTION

The present invention is related to the following co-pending US application: U.S. patent application Ser. No. 12/261,372, filed Oct. 30, 2008.

1. Field of the Invention

This invention relates, in general, to analytical devices and, in particular, to analytical test strips and associated methods.

2. Description of the Related Art

The determination (e.g., detection and/or concentration measurement) of an analyte in a fluid sample is of particular interest in the medical field. For example, it can be desirable to determine glucose, cholesterol, acetaminophen and/or HbA1c concentrations in a sample of a bodily fluid such as urine, blood or interstitial fluid. Such determinations can be achieved using analytical test strips, based on, for example, photometric or electrochemical techniques, along with an associated meter. For example, the OneTouch® Ultra® whole blood testing kit, available from LifeScan, Inc., Milpitas, USA, employs an electrochemical-based analytical test strip for the determination of blood glucose concentration in a whole blood sample.

Typical electrochemical-based analytical test strips employ a plurality of electrodes (e.g., a working electrode and a reference electrode) and an enzymatic reagent to facilitate an electrochemical reaction with an analyte of interest and, thereby, determine the concentration of the analyte. For example, an electrochemical-based analytical test strip for the determination of glucose concentration in a blood sample can employ an enzymatic reagent that includes the enzyme glucose oxidase and the mediator ferricyanide. Further details of conventional electrochemical-based analytical test strips are included in U.S. Pat. No. 5,708,247, which is hereby incorporated in full by reference.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention, in which.

DETAILED DESCRIPTION OF THE INVENTION

Figure 1:
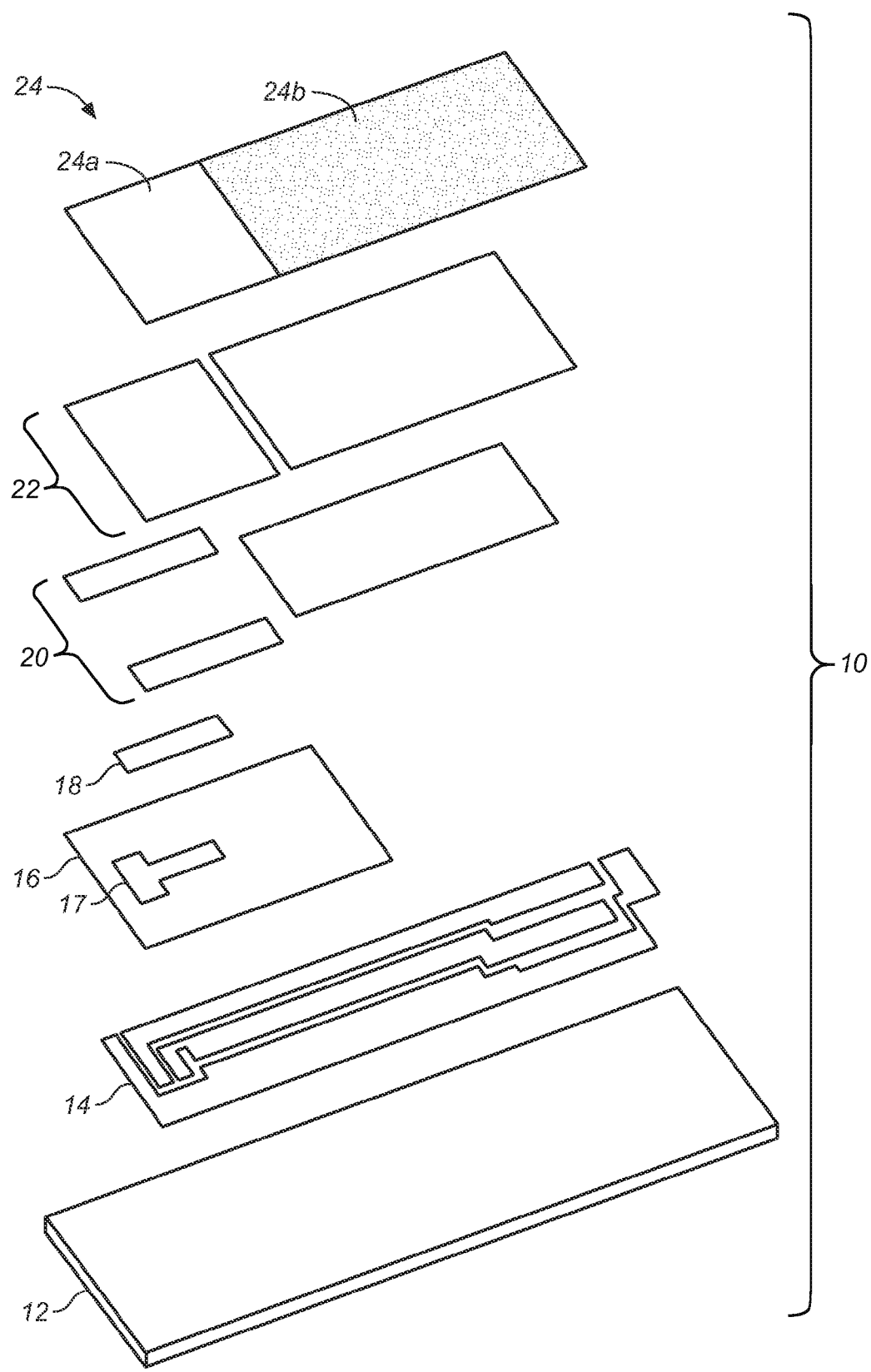
FIG. 1 is a simplified exploded perspective view of an electrochemical-based analytical test strip according to an exemplary embodiment of the present invention.

An analytical test strip according to the present invention includes a substrate, an enzymatic reagent layer (disposed, for example, over the substrate), and a top layer (with a first portion and an opaque second portion) disposed over the enzymatic reagent layer.

The analytical test strip also has a sample-receiving chamber defined therein. Moreover, the sample receiving chamber has a working portion and a non-working portion. The first portion (e.g., a transparent first portion or a translucent first portion) and the opaque second portion of the top layer are configured such that a user can view the working portion of the sample-receiving chamber through the first portion. Moreover, the user is precluded from viewing the non-working portion of the sample-receiving chamber by the opaque second portion.

Analytical test strips according to embodiments of the present invention can be configured, for example, as a photometric analytical test strip or as an electrochemical-based analytical test strip. An embodiment of an electrochemical-based analytical test strip according to the present invention includes an electrically-insulating substrate, a patterned conductive layer disposed over the electrically-insulating substrate, a patterned insulating layer disposed over the patterned conductive layer, an enzymatic reagent layer disposed at least over at least a portion of the patterned conductive layer, and a top layer (with a first portion and an opaque second portion) disposed over the enzymatic reagent layer.

The electrochemical-based analytical test strip also has a sample-receiving chamber defined therein. Moreover, the sample receiving chamber has a working portion and a non-working portion. The first portion (e.g., a transparent first portion or a translucent first portion) and the opaque second portion of the top layer are configured such that a user can view the working portion of the sample-receiving chamber through the first portion. Moreover, the user is precluded from viewing the non-working portion of the sample-receiving chamber by the opaque second portion.

Since a user can view only the working portion of the sample-receiving chamber, a user can readily visually verify when a bodily fluid sample has completely filled the working portion, thus providing for accurate analyte determination. It should noted that once apprised of the present disclosure, one skilled in the art will recognize that the working portion of the sample receiving portion is that portion that must be filled by a sample to enable accurate results during use of the analytical test strip, while filling of the non-working portion is not required for accurate results.

Since the opaque second portion blocks a user form viewing the non-working portion of the sample-receiving chamber, user visual verification is beneficially independent of whether the bodily fluid sample has or has not filled the non-working portion of the sample-receiving chamber. Therefore, a user is prevented from erroneously concluding that a sample fill-error has occurred when the working portion has been filled but the non-working portion has not been filled. This benefit leads to the first portion of the top layer also being referred to as a minimal fill-error sample viewing window. Further details, characteristics and benefits of such an analytical test strip are described with respect to the further embodiments discussed below.

Referring to FIGS. 1-5, an electrochemical-based analytical test strip 10 according to the present invention includes an electrically-insulating substrate 12, a patterned conductor layer 14, a patterned insulation layer 16, an enzymatic reagent layer 18, a patterned adhesive layer 20, a hydrophilic layer 22, and a top layer 24.

The disposition and alignment of patterning of electrically-insulating substrate 12, patterned conductor layer 14 (including reference electrode 14a, first working electrode 14b and second working electrode 14c), patterned insulation layer 16 (with electrode exposure window 17 extending therethrough) and enzymatic reagent layer 18, and patterned adhesive layer 20 (depicted by the outermost two vertical dashed lines in FIG. 4), hydrophilic layer 22 (not shown in FIG. 4) and top layer 24 of electrochemical-based analytical test strip 10 are such that sample receiving-chamber 26 is formed within electrochemical-based analytical test strip 10.

To ease manufacturing tolerances and provide for ready sample application and flow, the total volume of sample-receiving chamber 26 is greater than the minimal volume required for accurate use of electrochemical-based analytical test strip 10. Therefore, the sample-receiving chamber includes both a working portion that can hold the aforementioned minimal volume and a non-working portion that is the remainder of the sample-receiving chamber. A typical, but non-limiting, volume of the working portion for the embodiment of FIGS. 1-4 is approximately 0.95 micro-liters, while the typical, but non-limiting, volume of the total sample-receiving chamber is approximately 1.1 micro-liters. For these typical volumes the working portion constitutes approximately 86% of the sample-receiving chamber by volume.

Figure 4:
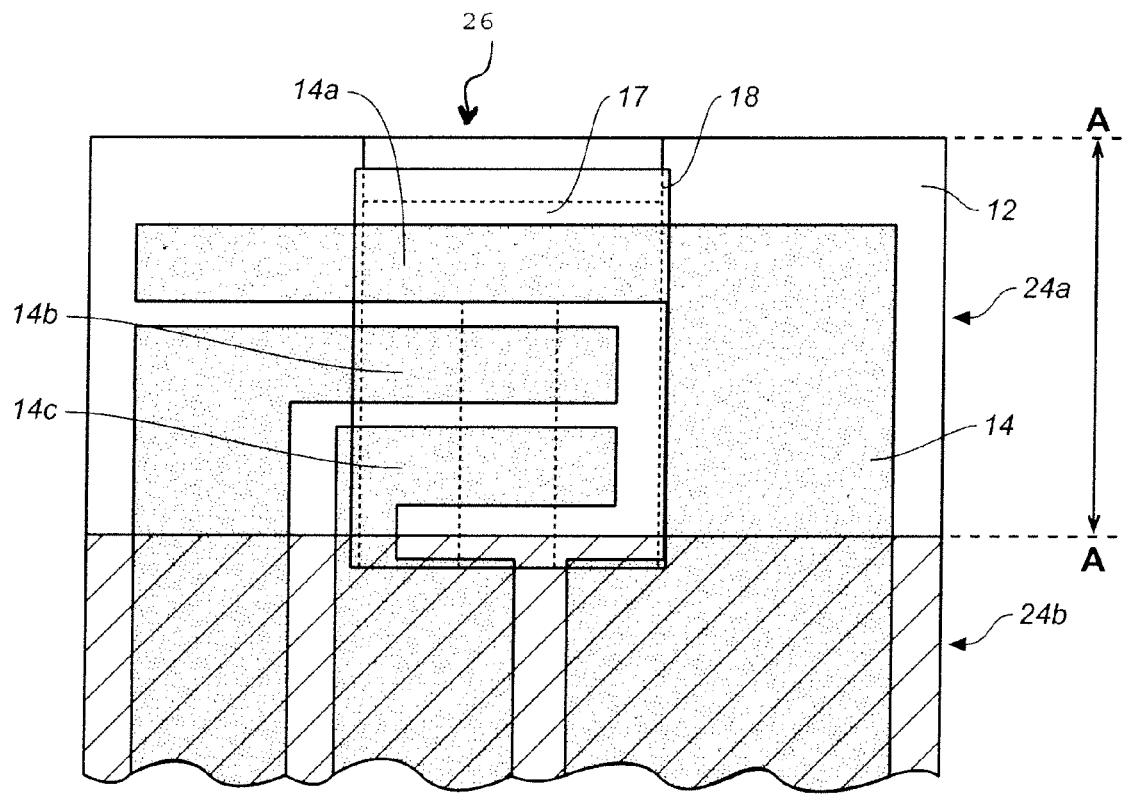
FIG. 4 is a simplified see-through top view of a portion of the electrochemical-based analytical test strip of FIG. 1 that depicts alignment of various components.

In the embodiment of FIGS. 1-4, the extent of the working portion is essentially defined by (i) the overlap of electrode exposure window 17 with reference electrode 14a, first working electrode 14b and second working electrode 14c of patterned conductor layer 14; (ii) slightly beyond the extent of the second working electrode 14c (to allow for manufacturing tolerances); and (iii) the underside extent of hydrophilic layer 22. Therefore, the working portion is essentially T-shaped in the perspective of FIG. 4 with a "height" depicted by line A-A in FIG. 4. The total sample-receiving chamber in the embodiment of FIG. 4 is essentially defined by the patterned adhesive layer and the hydrophilic layer.

Electrically-insulating substrate 12 can be any suitable electrically-insulating substrate known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, or a polyester substrate. The electrically-insulating substrate can have any suitable dimensions including, for example, a width dimension of about 5 mm, a length dimension of about 27 mm and a thickness dimension of about 0.5 mm.

Electrically-insulating substrate 12 provide structure to the strip for ease of handling and also serves as a base for the application (e.g., printing) of subsequent layers (e.g., a carbon-based patterned conductive layer). It should be noted that patterned conductor layers employed in analytical test strips according to embodiments of the present invention can take any suitable shape and be formed of any suitable materials including, for example, metal materials and conductive carbon materials.

Figure 2:
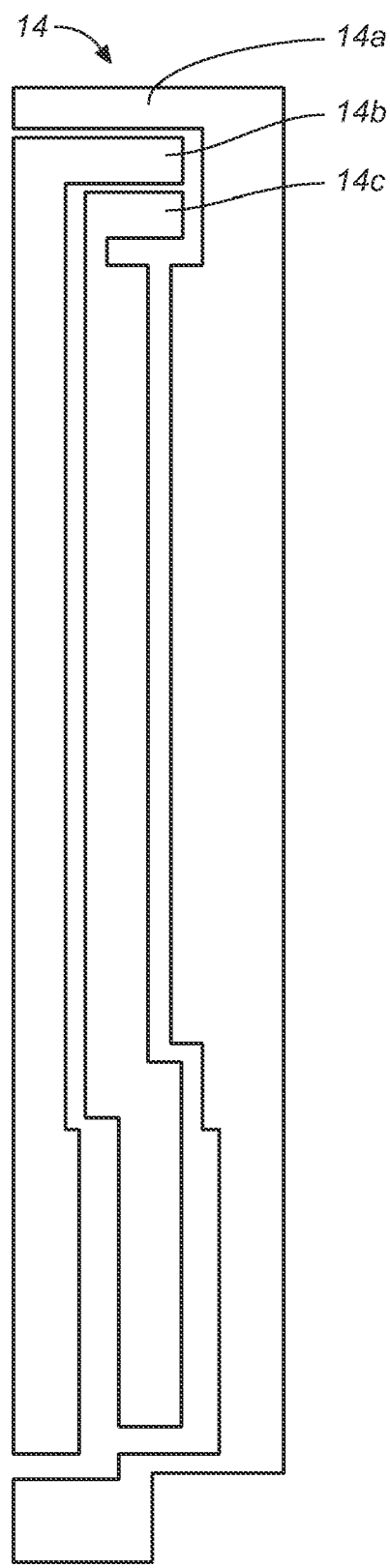
FIG. 2 is a simplified top view of the patterned conductive layer of the electrochemical-based analytical test strip of FIG. 1.
Figure 3:
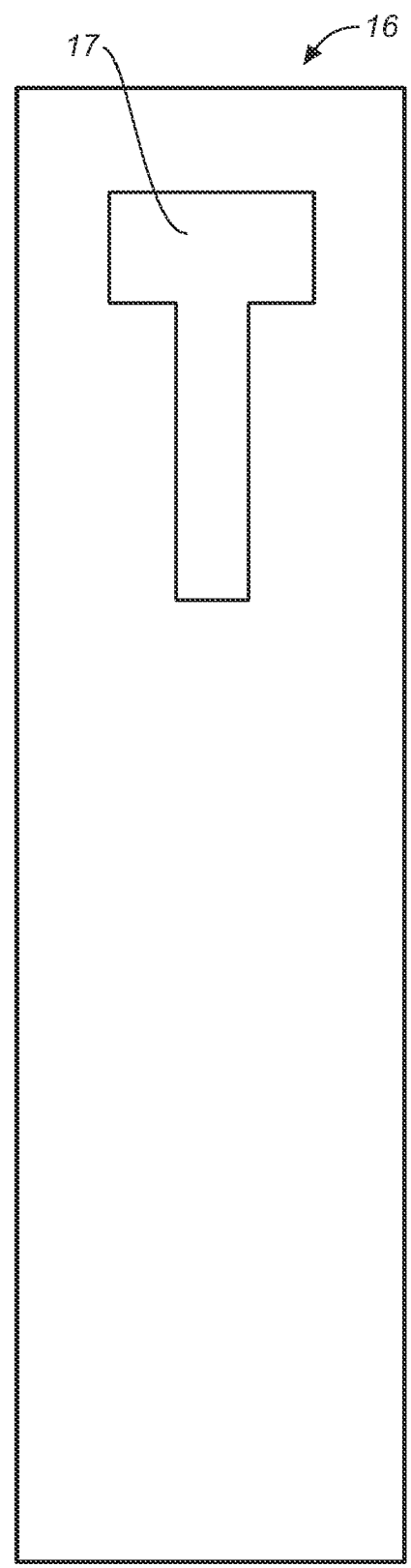
FIG. 3 is a simplified top view of the patterned insulating layer of the electrochemical-based analytical test strip of FIG. 1.

In the embodiment of FIGS. 1-4, patterned conductive layer 14 includes a counter electrode 14a (also referred to as a reference electrode), a first working electrode 14b, and a second working electrode 14c (see FIGS. 2 and 4 in particular). Although electrochemical-based analytical test strip 10 is depicted as including three electrodes, embodiments of electrochemical-based analytical test strips, including embodiments of the present invention, can include any suitable number of electrodes.

Counter electrode 14a, first working electrode 14b and second working electrode 14c can be formed of any suitable material including, for example, gold, palladium, platinum, indium, titanium-palladium alloys and electrically conducting carbon-based materials. Details regarding the use of electrodes and enzymatic reagent layers for the determination of the concentrations of analytes in a fluid sample, are in U.S. Pat. No. 6,733,655, which is hereby fully incorporated by reference.

Patterned insulation layer 16 can be formed, for example, from a screen printable insulating ink. Such a screen printable insulating ink is commercially available from Ercon of Wareham, Mass. U.S.A. under the name "Insulayer."

Patterned adhesive layer 20 can be formed, for example, from a screen-printable pressure sensitive adhesive commercially available from Apollo Adhesives, Tamworth, Staffordshire, UK. In the embodiment of FIGS. 1-4, patterned adhesive layer 20 defines outer walls of the sample-receiving chamber 26.

Hydrophilic layer 22 can be, for example, a clear film with hydrophilic properties that promote wetting and filling of electrochemical-based analytical test strip 10 by a fluid sample (e.g., a whole blood sample). Such clear films are commercially available from, for example, 3M of Minneapolis, Minn. U.S.A.

Enzymatic reagent layer 18 can include any suitable enzymatic reagents, with the selection of enzymatic reagents being dependent on the analyte to be determined. For example, if glucose is to be determined in a blood sample, enzymatic reagent layer 18 can include oxidase or glucose dehydrogenase along with other components necessary for functional operation. Enzymatic reagent layer 18 can include, for example, glucose oxidase, tri-sodium citrate, citric acid, polyvinyl alcohol, hydroxyl ethyl cellulose, potassium ferricyanide, antifoam, cabosil, PVPVA, and water. Further details regarding enzymatic reagent layers, and electrochemical-based analytical test strips in general, are in U.S. Pat. No. 6,241,862, the contents of which are hereby fully incorporated by reference.

Top layer 24 includes a first portion 24a (e.g. a transparent or translucent first portion) and an opaque second portion 24b. First portion 24a and the opaque second portion 24b of the top layer are configured and aligned with the remainder of the analytical test strip such that a user can view the working portion of the sample-receiving chamber through the first portion of the top layer and is precluded from viewing the non-working portion of the sample-receiving chamber by the opaque second portion of the top layer. This configuration prevents a user from erroneously determining that a sample fill error has occurred when the working portion of the sample-receiving chamber has been filled but the non-working portion has not been filled.

Top layer 24 can be, for example, a clear film, with opaque second portion 24b being created, for example, by overprinting of the clear film with an opaque ink and first portion 24a being simply clear film without overprinting. A suitable clear film is commercially available from Tape Specialities, Tring, Hertfordshire, UK.

Electrochemical-based analytical test strip 10 can be manufactured, for example, by the sequential aligned formation of patterned conductor layer 14, patterned insulation layer 16 (with electrode exposure window 17 extending therethrough), enzymatic reagent layer 18, patterned adhesive layer 20, hydrophilic layer 22 and top film 24 onto electrically-insulating substrate 12. Any suitable techniques known to one skilled in the art can be used to accomplish such sequential aligned formation, including, for example, screen printing, photolithography, photogravure, chemical vapour deposition and tape lamination techniques.

During use of electrochemical-based analytical test strip 10 to determine an analyte concentration in a fluid sample (e.g., blood glucose concentration in a whole blood sample), electrodes 14a, 14b and 14c of patterned conductor layer 14 are employed to monitor an electrochemical reaction induced current of interest. The magnitude of such a current can then be correlated with the amount of analyte present in the fluid sample under investigation. During such use, a bodily fluid sample is introduced into sample-receiving chamber 26 of electrochemical-based analytical test strip 10.

Figure 5:
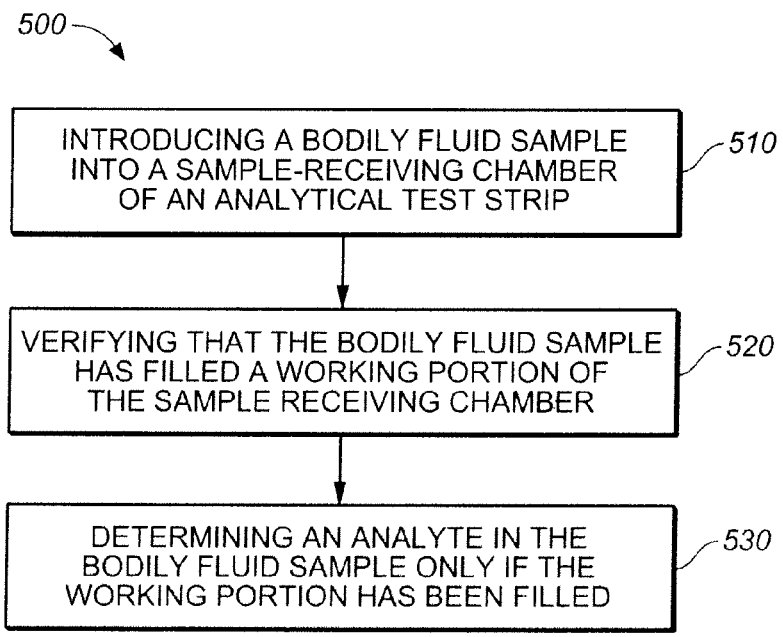
FIG. 5 is a flow chart of a process for determining an analyte in a bodily fluid sample according to an exemplary embodiment of the present invention.

FIG. 5 is a flow chart of a method 500 for determining an analyte (such a glucose) in a bodily fluid sample (e.g., a whole blood sample) according to an exemplary embodiment of the present invention. At step 510, method 500 includes introducing a bodily fluid sample into a sample-receiving chamber of an analytical test strip.

Method 500 also includes verifying that the bodily fluid sample has filled a working portion of the sample-receiving chamber by user visual observation of the working portion through a first portion of a top layer of the analytical test strip, while an opaque second portion of the top layer precludes user visual observation of a non-working portion of the sample-receiving chamber (see step 520 of FIG. 5). Thereafter, the concentration of analyte in the bodily fluid sample is determined (for example, using an associated meter) only if during the verifying step the user has verified that the bodily fluid sample has filled the working portion, as set forth in step 530.

Once apprised of the present disclosure, one skilled in the art will recognize that methods according to embodiments of the present invention, including method 500, can be conducted using analytical test strips according to the present invention, including the electrochemical-based analytical test strip of FIGS. 1-4.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. An analytical test strip comprising:
   a substrate;
   an enzymatic reagent layer;
   a top layer disposed over the enzymatic reagent layer, the top layer having a first portion and an opaque second portion; and
   a sample receiving chamber defined within the analytical test strip, the sample receiving chamber having a working portion configured to contain only a minimal volume of sample required for operation of the analytical test strip and a non-working portion configured to contain a remaining volume of sample beyond the minimal volume required for operation of the analytical test strip;
   wherein the first portion and the opaque second portion of the top layer are configured such that a user can view the complete working portion of the sample-receiving chamber through the first portion of the top layer and is precluded from viewing the non-working portion of the sample-receiving chamber by the opaque second portion of the top layer.

2. The analytical test strip of claim 1 wherein the analytical test strip is configured as a photometric analytical test strip.

3. The analytical test strip of claim 1 wherein the analytical test strip is an electrochemical-based analytical test strip and the substrate is an electrically-insulating substrate; the electrochemical-based analytical test strip further comprising:
   a patterned conductive layer disposed over the electrically-insulating substrate; and
   a patterned insulating layer disposed over the patterned conductive layer;
   and wherein the enzymatic layer is disposed at least over at least a portion of the patterned conductive layer.

4. The electrochemical-based analytical test strip of claim 3, wherein the top layer is an adhesive tape.

5. The electrochemical-based analytical test strip of claim 3 wherein the first portion of the top layer is transparent.

6. The electrochemical-based analytical test strip of claim 3 wherein the first portion of the top layer is translucent.

7. The electrochemical-based analytical test strip of claim 3 further including a patterned adhesive layer disposed over the enzymatic reagent layer.

8. The electrochemical-based analytical test strip of claim 3 wherein the working portion of the sample receiving chamber has a volume of approximately 0.95 micro-liters and the sample-receiving chamber has a volume of approximately 1.1 micro-liters.

9. The electrochemical-based analytical test strip of claim 3 wherein the working portion of the sample receiving chamber constitutes approximately 86 percent of the sample-receiving chamber.

10. The analytical test strip of claim 1 wherein the sample receiving chamber is configured for introduction of a whole blood sample.

* * * * *